United States Patent [19]
Patel et al.

[11] Patent Number: 4,886,651
[45] Date of Patent: Dec. 12, 1989

[54] PROCESS FOR CO-PRODUCTION OF HIGHER ALCOHOLS, METHANOL AND AMMONIA

[75] Inventors: Nitin M. Patel; Shoou-I Wang, both of Allentown, Pa.

[73] Assignee: Air Products and Chemicals, Inc., Allentown, Pa.

[21] Appl. No.: 195,576

[22] Filed: May 18, 1988

[51] Int. Cl.[4] .......................... C01C 1/04; C07C 29/15
[52] U.S. Cl. ................................... 423/359; 518/703; 518/704
[58] Field of Search .................. 423/359; 518/703, 704

[56] References Cited
U.S. PATENT DOCUMENTS

| | | | |
|---|---|---|---|
| 2,238,367 | 4/1941 | Mohr et al. | 518/703 |
| 3,598,527 | 8/1971 | Quartulli et al. | 423/361 |
| 4,315,900 | 2/1982 | Nozawa et al. | 423/359 |
| 4,367,206 | 1/1983 | Pinto | 423/359 |

FOREIGN PATENT DOCUMENTS
0180719 7/1985 European Pat. Off. ................ 29/32

OTHER PUBLICATIONS
"Ammonia" *Hydrocarbon Processing*, Nov. 1987, p. 64.
"Methanol" *Hydrocarbon Processing*, Nov. 1987, p. 79.
"Vinyl Acetate" *Hydrogen Processing*, Nov. 1987, p. 89.
"Catalytic Process for Producing Mixed Alcohols from Hydrogen and Carbon Monoxide".
PTC application 84/03696 filed Mar. 16, 1984, published Sep. 27, 1984.

*Primary Examiner*—Robert L. Stoll
*Assistant Examiner*—Wayne A. Langel
*Attorney, Agent, or Firm*—Geoffrey L. Chase; James C. Simmons; William F. Marsh

[57] ABSTRACT

An integrated process for producing higher alcohols, methanol and ammonia is set forth wherein two parallel reformations of methane are utilized to produce synthesis gas for the feed to the alcohol production and hydrogen for the ammonia production.

10 Claims, 1 Drawing Sheet

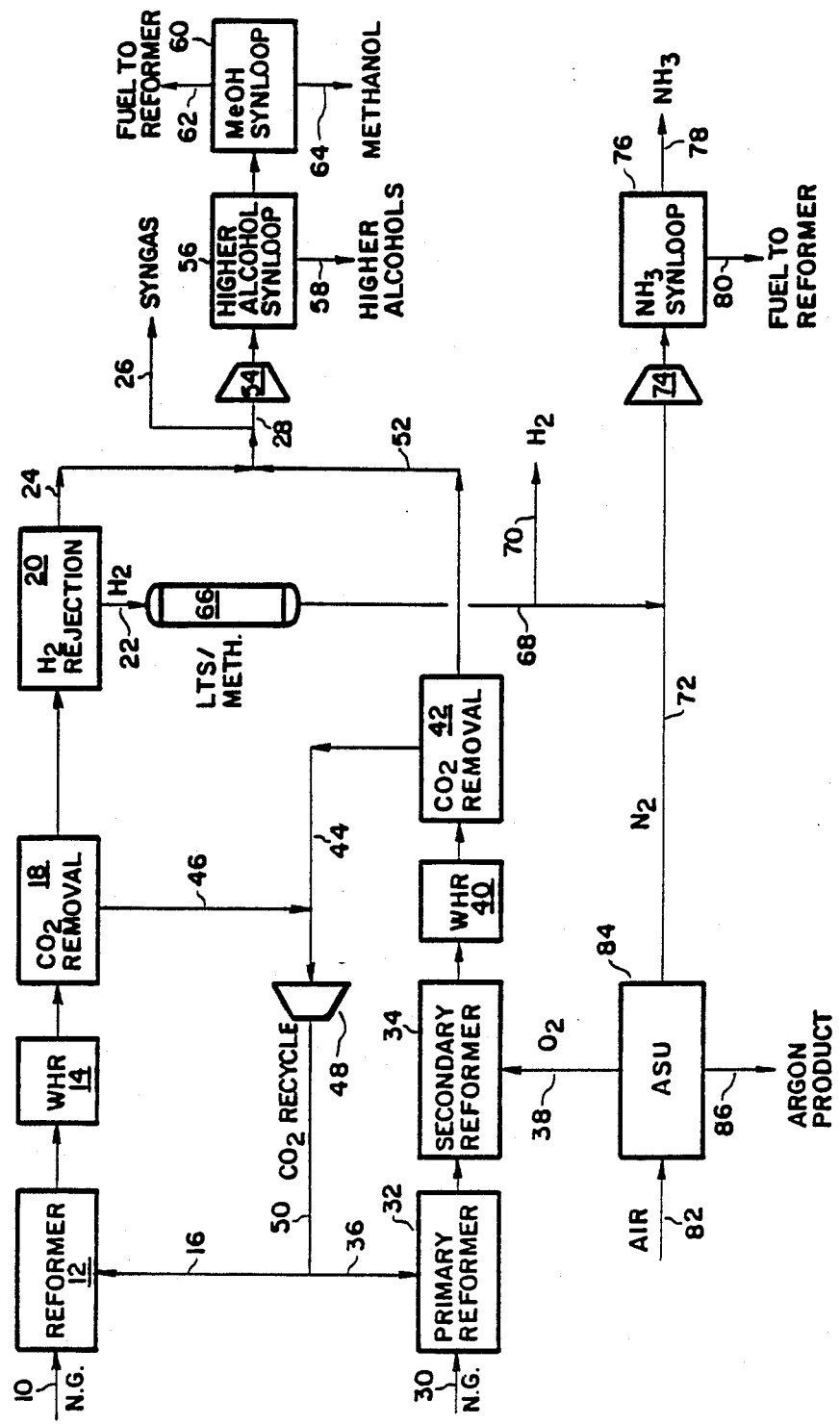

PROCESS FOR CO-PRODUCTION OF HIGHER ALCOHOLS, METHANOL AND AMMONIA

TECHNICAL FIELD

The process of the present invention is directed to the use of methane to synthesize methanol, lower alkanols and ammonia. Specifically, the process is related to the use of natural gas as a source for the synthesis of alcohols and ammonia using the integration of two trains of steam-methane reforming and air separation.

BACKGROUND OF THE PRIOR ART

Steam methane reforming to produce a hydrogen and carbon monoxiderich synthesis gas is well known in the prior art. In addition, it is known to use primary reformation for the catalytic conversion of methane and steam to produce hydrogen and carbon monoxide followed by secondary reforming in a thermal, partial oxidation of methane to produce a hydrogen and carbon monoxide-rich synthesis gas.

It is also known to produce alcohols by various processes including the catalytic reaction of methane to produce methanol.

Today the commercial production of higher alcohols ($C_3$ to $C_{13}$) is by the OXO process. In the OXO process, an olefin is reacted with gas in the presence of a cobalt or rhodium catalyst to produce an aldehyde that is one carbon atom longer than the olefin. The aldehyde is then reacted with hydrogen (hydrogenated) over a cobalt or nickel catalyst to produce an alcohol. Thus, in order to produce propanol, the olefin, ethylene, is fed to the process. The general form of the pertinent reactions are:

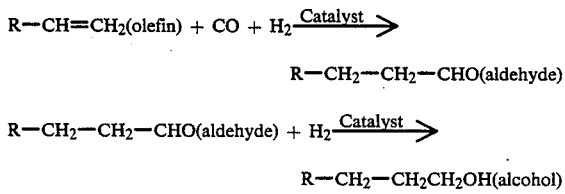

Drawbacks of this current OXO process are:

(i) It produces only from $C_3$ to $C_{13}$ alcohols. $C_1$ (methanol) and $C_2$ (ethanol) cannot be produced by this process, since olefin feeds of one carbon atom shorter length than the alcohols do not exist.

(ii) The process is dependent on olefin feedstock, which is not a stable compound in terms of availability and costs.

(iii) It is a complicated process involving two steps first to manufacture aldehyde from olefin and then hydrogenating the aldehyde to make alcohols.

For commercial production of $NH_3$, the synthesis gas which enters the ammonia synthesis loop is produced by reforming natural gas and steam in the primary reformer and in the secondary reformer where a proper (stoichiometric) amount of air is introduced. The raw reformer synthesis gas is further processed by two-stage carbon monoxide shift conversion followed by removal of carbon dioxide with MEA, carbonate or other physical adsorbent solution. Residual carbon oxides which are poisons to the ammonia synthesis catalyst are converted to methane via methanation.

The synthesis gas which enters the ammonia synthesis loop is relatively free of CO and $CO_2$, but contains impurities of methane and argon. These impurities are inerts in the ammonia synthesis process and must be purged to eliminate buildup in the synthesis loop. The purge results in a loss of valuable reactants, in addition to inerts. The buildup of inerts also results in a larger recycle stream requiring greater recompression and a larger sized synthesis reactor and loop.

The following attempts have been made in the past to overcome the drawbacks mentioned above.

(i) Currently, the production of $C_3$ through $C_{13}$ alcohols is divided into 96% by the OXO process, 4% by the Ziegler oligomerization process and only minor amounts by methanolysis of natural oils or fats. Methanol and ethanol are produced separately individually. The current state-of-the-art methanol process is the ICI low-pressure process, licensed by Imperial Chemical Industries PLC. Ethanol is produced by direct hydration of ethylene by the use of demineralized water, a process licensor is HULS AKTIENGELLSCHAFT, West Germany.

(ii) In the $NH_3$ process, the purge gas stream is treated to recover hydrogen which can be recyled back to the ammonia loop. This approach only solves the problem of loss of reactant in the purge. The purge stream can be sent through a membrane unit, cryogenic unit or PSA to recover hydrogen, all of which have been applied commercially in this service.

In contrast to these prior art processes, the process of the present invention provides an optimized technique for carbon monoxide-sourced production of higher alcohols, methanol and the hydrogen-sourced production of ammonia by integrating various unit operations of the synthetic route. The present invention allows the concise control of synthesis gas composition, most typically the hydrogen to carbon monoxide ratio, as required for the different product productions whereby flexibility and optimized plant efficiency is achieved. These advantages will be more clearly delineated below.

BRIEF SUMMARY OF THE INVENTION

The present invention is an integrated process for the production of higher alcohols, methanol and ammonia, comprising the steps of: catalytically reforming a first methane-containing stream with steam and carbon dioxide to form a first hydrogen and carbon monoxide-containing synthesis gas, removing carbon dioxide from said first synthesis gas and recycling at least a portion of the carbon dioxide to said reformation, rejecting at least a portion of the hydrogen content of said first synthesis gas to produce a first carbon monoxide-rich synthesis gas and a hydrogen stream, at least partially catalytically reforming a second methane-containing stream with steam and carbon dioxide to form an initial methane, hydrogen and carbon monoxide-containing synthesis gas and further reforming said initial synthesis gas by partial oxidation with an oxygen-enriched gas to result in a second hydrogen and carbon monoxide-containing synthesis gas, removing carbon dioxide from said second synthesis gas and recycling at least a portion of the carbon dioxide to said catalytic reformation, combining said hydrogen stream with a nitrogen-rich stream and catalytically reacting the combined stream to produce ammonia, combining said first and second synthesis gas streams and catalytically reacting them to produce higher alcohols and a purge stream of residual unreacted synthesis gas at an elevated pressure, and reacting said purge stream to produce methanol.

Preferably, the oxygen-enriched gas is commercially pure oxygen having an oxygen content of at least 95%, optimally 99.5%. Such an oxygen-enriched gas can be produced by traditional air separation processes such as cryogenic, sorptive or membrane techniques, wherein a nitrogen-enriched gas is also produced which may be utilized in the ammonia synthesis.

Preferably, the hydrogen stream is rejected from said first synthesis gas by a membrane selected for the rejection of hydrogen over carbon monoxide.

Preferably, the combined first and second synthesis gas streams have a hydrogen to carbon monoxide mole ratio in the range of 1.5 up to 3.0.

Preferably, the hydrogen stream is subjected to low temperature water gas shift reaction and methanation to eliminate any residual carbon monoxides in the hydrogen stream.

Preferably, the higher alcohols include methanol, ethanol, propanol, butanol, pentanol and their isomers.

Preferably, the carbon dioxide removed from the reformation streams is combined and recycled to each reformation as required to maximize the production of low hydrogen to carbon monoxide ratio synthesis gas.

BRIEF DESCRIPTION OF THE DRAWING

The drawing is schematic illustration of a preferred embodiment of the present invention.

DETAILED DESCRIPTION OF THE INVENTION

The present invention provides an optimized process cycle for co-production of higher alcohols, methanol and ammonia by integrating various process unit operations. Since each different product requires specific feed gas composition for optimization, the present invention by properly selecting and integrating the various unit processes provides an efficient and flexible integrated process operation, which produces various products under optimized conditions. Additionally, the present invention is not dependent on olefin feedstocks which suffer from variable costs and changes in availability, but rather the present invention utilizes methane-containing gases, such as natural gas, which is generally very stable with regard to worldwide availability and costs. Specifically, the integration of three separate product synthesis unit operations achieves better utilization of carbon and hydrogen sourced from the hydrocarbon feedstock to the overall process.

The present invention utilizes two steam-methane reformation process trains. In one steam-methane reformation with total carbon dioxide recycle, the process unit operation is designed so that hydrogen can be removed from the product and the unit operation still results in a optimized synthesis gas composition for a higher alcohol production. A second steam-methane reformation with total carbon dioxide recycle is coupled with an oxygen-fed secodary reformation step to produce a synthesis gas which is directly amenable as an optimized feed for higher alcohol production which requires a minimum hydrogen to carbon monoxide ratio. The oxygen is supplied by an air separation unit which also supplies an argon byproduct and a nitrogen feed for an ammonia synthesis plant. A hydrogen rejection process stage is used in the first steam-methane reformation process train to optimize the total syngas composition by making it rich in carbon monoxide and also to produce the raw hydrogen for feed to the ammonia production process stage. The synthesis gas product of both steam-methane reformation process trains are combined to result in a synthesis gas containing a hydrogen to carbon monoxide mole ratio of 1.5 to 3.0, which is desired for use in higher alcohol production. The unreacted purge gas from the higher alcohol synthesis process stage is available at elevated pressure and appropriate stoichiometry to be used as feed to an methanol synthesis process stage for production of methanol. The hydrogen stream may be further purified by low temperature shift reaction to produce additional hydrogen and methanation to convert carbon oxides to methane before being utilized as feed with nitrogen from the air separation unit for ammonia synthesis in the ammonia synthesis process stage.

The process will now be described in greater detail with reference to the drawing. A methane containing stream, such as natural gas, introduced in line 10 at a temperature of 750° F. and a pressure of 116 psia into the first reformer 12 for catalytic reformation with steam, which is introduced but not illustrated, and with recycle carbon dioxide 16 to be catalytically reformed over a nickel on alumina catalyst to produce a hydrogen and carbon monoxide-enriched synthesis gas. The carbon dioxide recycle lowers the hydrogen to carbon monoxide ratio of the synthesis gas and provides better overall utilization of all of the carbon coming into the process. The resulting synthesis gas is cooled in a waste heat recovery boiler 14 which produces process steam from boiler feed water. This stream is then at a temperature of 110° F. and a pressure of 88 psia. The stream contains approximately 7% residual carbon dioxide contamination, which is removed in the carbon dioxide removal zone 18 for recycle in line 46. The carbon dioxide removal zone 18 can comprise a chemical solvent absorption and stripping cyclic process, as is well known in the prior art utilizing monoethanolamine (MEA). The MEA is regenerated with steam stripping.

The carbon dioxide depleted first synthesis gas is then subjected to hydrogen rejection in the hydrogen rejection zone 20 which can comprise a membrane which is selective to the rejection of hydrogen over carbon monoxide. The synthesis gas entering the hydrogen rejection zone 20 has 73% hydrogen which is reduced to 58% upon emanating from the hydrogen rejection zone 20 in line 24. It is apparent that the membrane selectivity does not require a high selectivity characterization, because only a portion of the hydrogen content of the first synthesis gas stream is required to be rejected to produce the first carbon monoxide-enriched synthesis gas in line 24. The rejected hydrogen-rich stream in line 22 is then subjected to low temperature shift using a catalyst of copper oxide supported on zinc oxide and/or alumina to produce additional hydrogen by water gas shift reaction, producing $H_2$ and carbon dioxide. The residual carbon dioxide previously existing in the hydrogen stream and the carbon dioxide produced by low temperature shift is eliminated by methanation wherein hydrogen is reacted with the carbon dioxide and any carbon monoxide over a catalyst of nickel on alumina to produce methane and water. The low temperature shift and methanation occurs in reaction zone 66.

An additional stream of methane-rich gas, such as natural gas, is introduced in line 30 at a temperature of 734° F. and a pressure 406 psia into a second steam-methane reformation zone 32 along with steam, which is not illustrated, and recycled carbon dioxide from line 36. The carbon dioxide in the second steam-methane reformation zone 32 achieves the same result as the first steam-methane reformation, which is to say that the carbon dioxide recycle utilizes the full extent of carbon introduced as feed and depresses the hydrogen to carbon monoxide ratio favorably.

The effluent from the second steam-methane reformation zone 32 contains residual methane of up to 13% which is further reacted with oxygen in a secondary reformation zone 34, wherein partial oxidation is achieved with oxygen in line 38, which comprises commercially pure oxygen at a temperature of 824° F. and a pressure of 370 psia. This oxygen can be produced from an air feed in line 82 to an air separation unit 84 comprising a traditional cryogenic distillation column or alternatively an adsorptive or membrane separation system. Preferably, a distillation column would allow for the simultaneous recovery of an argon product 86 and a nitrogen product in line 72, which latter stream may be utilized in the ammonia synthesis process stage to be discussed below.

The use of primary reformation comprising steam-methane reformation in conjunction with secondary reformation comprising partial oxidation results in a second synthesis gas stream having a desirably low hydrogen to carbon monoxide ratio. This stream is removed at a temperature of 1,842° F. and a pressure of 363 psia to be cooled with the production of steam from boiler feed water in waste heat recovery boiler 40. The second hydrogen and carbon monoxide-containing synthesis gas stream exiting the waste heat recovery boiler 40 is at a temperature of 238° F. and a pressure 332 psia. The second synthesis gas stream contains approximately 15% carbon dioxide which is removed in the carbon dioxide removal zone 42, which may comprise a monoethanolamine chemical absorption unit. The monoethanolamine absorbent preferentially absorbs carbon dioxide out of the synthesis gas and is regenerated by steam stripping and recycle to the adsorption zone, as is traditionally done with such a system. Other chemical absorbents or solvents can be contemplated. The carbon dioxide is removed in line 44 and combined with the carbon dioxide previously recovered in the discussion of the first reformation process train recovered in line 46. The combined carbon dioxide is compressed in compressor 48. The recycling carbon dioxide in line 50 is split into stream 16 returned to the first reformation process train and a stream 36 recycled to the second reformation process train.

The second synthesis gas stream in line 52 is combined with the first synthesis gas stream in line 24 to produce a combined synthesis gas stream in line 28. A portion of the synthesis gas can be removed as a product in line 26. The combined synthesis gas stream is compressed in compressor 54 to a pressure of 4,750 psia and a temperature of 205° F. The combined stream has a hydrogen to carbon monoxide ratio of approximately 1.5.

This combined synthesis gas stream is then introduced into the higher alcohol synthesis zone 56 wherein it is catalytically reacted to produce higher alcohols including methanol, ethanol, propanol, butanol and pentanol by the following reactions:

$$CO + 2H_2 \rightarrow CH_3OH$$

$$CO_2 + 3H_2 \rightarrow CH_3OH + H_2O$$

$$3CO + 3H_2 \rightarrow C_2H_5OH + CO_2$$

$$5CO + 4H_2 \rightarrow C_3H_7OH + 2CO_2$$

$$7CO + 5H_2 \rightarrow C_4H_9OH + 3CO_2$$

$$9CO + 6H_2 \rightarrow C_5H_{11}OH + 4CO_2$$

The higher alcohol synthesis zone 56 performs a reaction of the Fischer-Tropsch type to form alcohols from hydrogen and carbon monoxide using a catalyst containing at least one element selected from the group consisting of molybdenum, tungsten, iridium and mixtures thereof in free or combined form, as well as a promoter comprising an alkali or alkaline earth element in free or combined form which may be on a suporot when the reaction is operated at relatively low elevated temperatures and fairly high pressures to result in the appropriate alcohols. Generally the selectivity to alcohols is dependent on the pressure. In the normal operating ranges, the higher the pressure at a given temperature the more selective the process will be to higher alcohols. The minimum pressure should be 500 psig. The desired pressure range is from 1,500 to 4,000 psig with a maximum usually at 5,000 psig. Although minimum temperatures are dedired and the minimum elevated temperature should be no lower than 200° C. The space velocity of hydrogen and carbon monoxide gas at standard temperature and pressure should be in the range of 100 to 10,000 hrs.$^{-1}$. Preferably 300 to 5,000 hrs.$^{-1}$. A portion of the unreacted hydrogen and carbon monoxide may be recycled, although no recycle is required. The molybdenum, tungsten or iridium may be present in the catalyst in free or combined form, which means that it may be present as a metal, an alloy or a compound of the element. Representative compounds include the sulfides, carbides, oxides, halides, nitrides, borides, salicylides, oxyhalides, carboxylates such as acetates, acetile, acetonates, oxylates, etc., carbonyls and the like. Representative compounds also include the elements in an ionic form such as molybdates, phosphomolybdates, tungstates, phosphotungstates and the like and include the alkali, alkaline earth, rare earth and actinide series salts of these anions. The sulfides, carbonyls, carbides and oxides are preferred, with the sulfide being most preferred. The molybdenum, tungsten or iridium may be present in the amount based on the weight of the total catalyst of at least 2%, preferably at least 5% with an upper limit of 70%, preferably 30% of the total catalyst when the catalyst is supported. The second component of the catalyst is the promoter. The promoter may consist essentially of one or more alkali elements or alkaline earth elements in free or combined form. Alkali elements include lithium, sodium, potassium, rubidium, and cesium. Alkaline earth elements include: beryllium, magnesium, calcium, strontium and barium. Alkali elements and in particular sodium and potassium are preferred. Potassium is most preferred. The promoter may be present in free or combined form as a metal, oxide, hydroxide, sulfide or as a salt or combination of these. The alkaline promoter is preferably present at a level sufficient to render the support or the bulk catalyst neutral or basic. The promoter is generally present based on the weight of the finished catalyst in an amount of at least 0.05 wt. % as a free element in the finished catalyst. Preferably, it is present in an amount of at least 0.1% and most preferably at least 0.5%. Large amounts up to 20% of the promoter may be present. Preferably the promoter is present at less than 10%.

The production of the higher alcohol synthesis in zone 56 comprises the higher alcohols removed in line 58, as well as an unreacted stream removed to the methanol synthesis zone 60. The higer alcohols in line 58 are comprised of 23% methanol, 23% ethanol, 5% propanol, 1% butanol, 0.5% pentanol with residual methyl and ethyl acetate, as well as greater amounts of water, carbon dioxide, carbon monoxide, hydrogen and methane. These individual components can be separately recovered by known techniques, such as distillation columns and extraction columns, which are not the subject of the present invention.

The methanol synthesis stage 60 comprises a pressure vessel, which holds a single continuous bed of catalyst. The catalyst will be a copper/zinc onn alumina and the reaction conditions will be in the range of 940 to 970 psig and a temperature in the range of 100° to 520° F. preferably 460° to 500° F. The reactions to produce methanol are between hydrogen and carbon monoxide or carbon dioxide and represented by the following chemical equations:

$$2H_2 + CO \rightarrow CH_3OH$$

$$3H_2 + CO_2 \rightarrow CH_3OH + H_2O$$

An ideal synthesis gas for methanol production should have a hydrogen content equal to twice the carbon monoxide content plus three times its carbon dioxide content. In practice a ratio of about 1.02 is used to account for carbon monoxide and carbon dioxide that dissolves in the exiting crude methanol. Accordingly the stoichiometry for an ideal synthesis gas for the methanol production is:

$$(2CO + 3CO_2)/H_2 = 1.02$$

The methanol synthesis reactions are strongly exothermic in nature and although they are limited by equalibrium and reaction rate, the temperature rise in the converter must be moderated. Too high an operating temperature can lead to catalyst sintering, which will cause some irreversible loss of activity. Temperature control is achieved by injecting warm-shot gas at appropriate levels directly into the catalyst bed using especially developed distributors, known as lozenges. These distributors or lozenges provide excellent gas mixing, while allowing free flow of catalyst between them, thus allowing rapid catalyst charging and discharging. Because the equilibrium constant for methanol formation is small, the amount of methanol made on a per-pass basis is small, necessitating a continuous recycle of reaction gas. Since both of the aforementioned reactions are reversible, methanol and water vapor in the converter exit gas should be condensed and separated as thoroughly as possible from the recycled loop gas. Thus, the concentration of methanol and the circulated gas returned to the converter is kept low to give the maximum driving force necessary for the synthesis reaction to take place. The crude methanol produced from the methanol synthesis stage 60 can be purified by extraction and distillation and removed as a methanol product from the process. The feed to the methanol synthesis stage 60 comprises 44.5% hydrogen, 27.7% carbon monoxide, 24% methane and residual amounts of carbon dioxide, ethane and nitrogen. The feed is at a pressure of 962 psia and 100° F. The methanol product derived in line 64 is approximately 99% methanol at a pressure of 90 psia and a temperature of 93.8° F. A purge stream in line 62 can be removed for fuel use to heat the reformers 12 and 32 and comprises a mixture of hydrogen, carbon monoxide, methane and alcohols.

The ammonia synthesis process stage 76 comprises a traditional ammonia synthesis reactor wherein extensive recycle is required because of the low equilibrium conditions of the ammonia reactors. The ammonia is recovered by condensation, with the unreacted hydrogen and nitrogen being recycled for further passes through the reactor. The reactor provides for the reversible ammonia synthesis reaction of hydrogen and nitrogen by the following formula:

$$N_2 + 3H_2 \rightarrow 2NH_3$$

This reaction is catalyzed by metallic iron, usually magnetite, that has been promoted with other oxides. The inlet feed gas preferably operates at a hydrogen to nitrogen mole ratio of 3:1 however some ratios below that level have been favorable. The hydrogen in line 68 which has been subjected to low temperature shift and methanation is directed to the ammonia synthesis process stage 76. A portion of excess hydrogen may be removed for export in line 70. Nitrogen is made available by separating air feed in line 82 to an air separation unit 84, which is preferably a cryogenic distillation unit which provides oxygen in line 38 and argon in line 86. The nitrogen in line 72 is combined with the hydrogen in line 68 and is compressed to feed conditions in compressor 74. The feed is at a pressure of 5,115 psia and a temperature of 90° F. This feed is 74.9% hydrogen and 25% nitrogen with residual methane and water. The hydrogen to nitrogen ratio is 3. The feed is cyclicly reacted in the ammonia synthesis process stage 76 in a traditional manner over an appropriate iron catalyst at a temperature in the range of 300 to 500° F. and a pressure in the range of 2000-5000 psi. The ammonia product in line 78 is 99.9% pure ammonia at a temperature of 50° F. and a pressure of 265 psia. A fuel stream is removed as a purge in line 80 comprising predominantly hydrogen with some nitrogen and methane. This stream is removed at 240 psia and 100° F.

As can be seen, the present invention integrates a number of discreet process stages to provide for a unique integration of conditions and product slates which are appropriately tailored for optimization of the processes stages operated in tandem. For instance, a first steam-methane reformation process train is operated in a traditional manner to produce sufficient hydrogen in its hydrogen and carbon monoxide synthesis gas so that some hydrogen may be rejected for use in ammonia synthesis, while retaining an appropriate hydrogen and carbon monoxide synthesis gas sufficient for alcohol production. A second train of steam-methane reformation is conducted with a primary and secondary reformer, which diminishes the hydrogen to carbon monoxide ratio for direct utilization in an alcohol synthesis stage, wherein hydrogen removal is not necessary for the ammonia synthesis gas. This second steam-methane reformation process train utilizes pure oxygen in its partial oxidation secondary reformer rather than the traditional air so as to avoid the requirements for nitrogen separation and segregation when fed to the higher alcohol synthesis stage. The second reformer is supplied with pure oxygen from an air separation unit, which is also capable of supplying the necessary nitrogen to the hydrogen rejected from the first steam-methane reformation process train, resulting in the appropriate 3:1 mole ratio of hydrogen to nitrogen for optimum conversion in the ammonia synthesis process stage. The resulting hydrogen/carbon monoxide synthesis gas, having a ratio in the range of 1.5 to 3.0, is well tailored for conversion in a higher alcohol synthesis process stage which allows for alcohols in the methanol to pentanol range to be produced by a stable feedstock of natural gas rather than olefins. The unreacted feed from the higher alcohol synthesis process stage is an acceptable feed for the traditional methanol synthesis process stage to produce additional methanol over that which is produced in the higher alcohol synthesis process stage. As can be seen, this unique integration provides desirable aspects for all of the individual process stages of the overall process configuration. With the production of various products in the synthetic process, including: higher alcohols, methanol and ammonia as well as byproducts of argon synthesis gas and hydrogen, the process allows flexibility to make a varied product slate and provides high efficiency in the production or the synthetic products wherein better utilization of carbon and hydrogen from the hydrocarbon feedstock is achieved.

The present invention has been set forth with regard to a preferred embodiment, however the scope of the present invention should be ascertained from the claims which follow.

What is claimed is:

1. An integrated process for the production of higher alcohols, methanol and ammonia comprising the steps of:
    (a) catalytically reforming a first methane-containing stream with steam and carbon dioxide to form a first hydrogen and carbon monoxide-containing synthesis gas;
    (b) removing carbon dioxide from said first synthesis gas and recycling at least a portion of the carbon dioxide to said reformation;
    (c) rejecting at least a portion of the hydrogen content of said first synethsis gas to produce a first carbon monoxide-rich synthesis gas and a hydrogen stream;
    (d) at least partially catalytically reforming a second methane-containing stream with steam and carbon dioxide to form an initial methane, hydrogen and carbon monoxide-containing synthesis gas and further reforming said initial synthesis gas by partial oxidation with an oxygen-enriched gas to result in a second hydrogen and carbon monoxide-containing synthesis gas;
    (e) removing carbon dioxide from said second synthesis gas and recycling at least a portion of the carbon dioxide to said catalytic reformation of step (d);
    (f) combining said hydrogen stream with a nitrogen-rich stream and catalytically reacting the combined stream to produce ammonia;
    (g) combining said first and second synthesis gas streams and catalytically reacting them to produce higher alcohols and a purge stream of residual unreacted synthesis gas at an elevated pressure; and
    (h) reacting said purge stream to produce methanol.

2. The process of claim 1 wherein said oxygen-enriched gas is commercially pure oxygen.

3. The process of claim 1 wherein said oxygen-enriched gas and said nitrogen-enriched stream are produced from an air separation process.

4. The process of claim 1 wherein said hydrogen stream is rejected from said first synthesis gas by a membrane selective for the rejection of hydrogen over carbon monoxide.

5. The process of claim 1 wherein said combined first and second synthesis gas streams have a hydrogen to carbon monoxide mol ratio in the range of 1.5 to 3.0.

6. The process of claim 1 wherein said hydrogen stream is subjected to low temperature water gas shift and methanation to eliminate any residual carbon oxides.

7. The process of claim 1 wherein the removed carbon dioxide of the two catalytic reformations is combined and recycled to said reformations to maximize low hydrogen to carbon monoxide ratios.

8. The process of claim 1 wherein an unreacted hydrogen-containing stream from the ammonia reaction is used as fuel for heating the catalytic reformations.

9. The process of claim 1 wherein unreacted synthesis gas from the methanol reaction is used as fuel for heating the catalytic reformations.

10. The process of claim 1 wherein a portion of the hydrogen gas of step (c) is exported from the process.

* * * * *